United States Patent [19]
> Christensen et al.

[11] 3,943,153

[45] Mar. 9, 1976

[54] (−)(CIS-1,2-EPOXY PROPYL)PHOSPHONIC ACID AMIDES

[75] Inventors: Burton G. Christensen, Scotch Plains; Michael W. Fordice, Clark; David B. R. Johnston, Warren, all of N.J.

[73] Assignee: Merck & Co., Inc., Rahway, N.J.

[22] Filed: Aug. 8, 1969

[21] Appl. No.: 848,678

Related U.S. Application Data

[63] Continuation-in-part of Ser. Nos. 758,149, Sept. 6, 1968, abandoned, and Ser. No. 760,684, Sept. 18, 1968, abandoned.

[52] U.S. Cl............................ 260/348 R; 424/278
[51] Int. Cl.²................ C07D 303/46; C07D 303/00
[58] Field of Search......................... 260/348 R, 551

[56] References Cited
UNITED STATES PATENTS

| | | | |
|---|---|---|---|
| 3,463,813 | 8/1969 | Dickerson............................ | 260/551 |
| 3,485,897 | 12/1969 | Jenker............................... | 260/348 R |
| 3,496,080 | 2/1970 | Harris................................. | 204/158 |
| 3,520,907 | 7/1970 | Taylor et al..................... | 260/348 R |
| 3,522,303 | 7/1970 | Ulrich................................ | 260/551 |

*Primary Examiner*—Richard J. Gallagher
*Assistant Examiner*—Jose Tovar
*Attorney, Agent, or Firm*—Hesna J. Pfeiffer; J. Jerome Behan

[57] ABSTRACT

Amides and thioates of (−)(cis-1,2-epoxypropyl)-phosphonic acid and phosphonothioic acid are prepared by converting (−)(cis-1,2-epoxypropyl)phosphonic acid or phosphonothioic acid or a salt thereof to an acid halide and reacting the acid halide with an amine, and by reacting the phosphonic acid or a salt thereof with an amine in the presence of a carbodiimide. The novel (−)(cis-1,2-epoxypropyl)phosphonic and phosphonothioic amides are active antibacterial agents.

3 Claims, No Drawings

(−)(CIS-1,2-EPOXY PROPYL)PHOSPHONIC ACID AMIDES

CROSS REFERENCES TO RELATED APPLICATIONS

This is a continuation-in-part of Ser. No. 758,149 filed Sept. 6, 1968 and Ser. No. 760,684 filed Sept. 18, 1968, both now abandoned.

BACKGROUND OF THE INVENTION

Although many valuable antibiotics are known for the treatment of various diseases, many of the known antibiotics are, in general, active against a limited number of pathogens. When certain strains of these pathogens develop resistance to a particular antibiotic, the antibiotic is rendered inactive against such resistant strains. Because of this development with regard to known antibiotics, the search continues in an effort to discover new antibacterial agents which are active against a wide range of pathogens and, in particular, against those strains of pathogens which are resistant to the known antibiotics.

DESCRIPTION OF THE PREFERRED EMBODIMENTS

The present invention relates to compounds which have significant antibacterial activity and to processes for preparing them. The compounds which are the subject of this invention are novel amides of (−)(cis-1,2-epoxypropyl)phosphonic acid and phosphonothioic acid. These novel derivatives can be represented by the following formula:

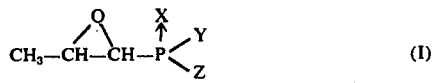
(I)

where X represents oxygen or sulfur, Y represents $-NR_1R_2$,

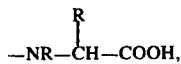

$-NROR$, $-NRNR_1R_2$, $-NR-N=CR_1R_2$,

$-N=C=X$, or $-N_3$, and Z represents Y, OR, SR or halogen wherein R is hydrogen or a hydrocarbyl or substituted hydrocarbyl group; and $R_1$ and $R_2$ represent hydrogen, acyl, or a hydrocarbyl or substituted hydrocarbyl group. Also included in Formula I are the inorganic and organic salts of those compounds where Z is $-OH$ or $-SH$, and the cyclic derivatives where Y and Z are connected via a residue of a polyfunctional hydrocarbyl compound such as a straight or branched chain alkylene, aralkylene, and arylene polyamine, and aminoalcohol and the like such as ethylenediamine, monoethanolamine, phenylenediamine, naphthalenediamine, o-aminophenol and the like and those cyclic derivatives where $-NR_1R_2$ represents the residue of a cyclic primary or secondary amine such as, for example, morpholine, piperidine, or pyrrolidine.

Where R, $R_1$ or $R_2$ in Formula I represent a hydrocarbyl or substituted hydrocarbyl radical, such radical can be an aliphatic, cycloaliphatic, araliphatic, aromatic or heterocyclic radical which can, if desired, be further substituted. Thus, for example, it can be aliphatic, such as substituted or unsubstituted alkyl, alkenyl or alkynyl, representative examples of which are alkyl such as methyl, propyl, isopropyl, t-butyl, hexyl, octyl, decyl, dodecyl, haloalkyl such as chloroethyl, fluoropropyl, bromoethyl and dichloroethyl, acylamidoalkyl such as acetylaminomethyl, phthalimidomethyl and benzoylaminoethyl, acyloxyalkyl such as benzoyloxymethyl, acetoxymethyl, pivaloyloxymethyl, propionoxyethyl, carboxymethyl and benzyloxyethyl, hydroxypropyl, piperidinomethyl, aminomethyl, aminoethyl, alkylaminoalkyl such as dimethylaminomethyl, diethylaminopropyl, and carboalkoxymethyl, cyanoethyl, sulfonamidoethyl and methoxymethyl, alkenyl such as allyl, methallyl, vinylpropenyl, hexenyl, octadienyl, alkynyl such as propargyl, ethynyl or chloroethynyl, cycloalkyl such as cyclohexyl, cyclohexenyl or cyclopropyl. When R, $R_1$ or $R_2$ is aliphatic, it preferably has from 1–6 carbon atoms, i.e. substituted or unsubstituted loweralkyl or alkenyl.

Examples of R, $R_1$ and $R_2$ representing an araliphatic radical are those cases where it is aralkyl or substituted aralkyl such as benzyl, phenethyl, phenylpropyl, p-halobenzyl and o-, m- or p-alkoxybenzyl, nitrobenzyl, aminophenethyl, pyridylethyl, nitrofurylmethyl, thienylpropyl and the like.

R, $R_1$ and $R_2$ also represents an aryl or substituted aryl radical such as phenyl, naphthyl or substituted phenyl, e.g. p-chlorophenyl, o-nitrophenyl, o,p-dihalophenyl, phenacyl, cyanophenyl, methoxyphenyl, p-sulfonamidophenyl and N′ derivatives thereof such as p(N-2-thiazolyl)sulfonamidophenyl, etc., aminophenyl, tolyl and the like, and preferably a mononuclear aromatic or substituted aromatic residue such as pyridyl, furyl, nitrofuryl, thienyl, thiazolyl, or pyrazinyl, or alternatively it can represent a hydrogenated hetero ring such as tetrahydrofuryl, tetrahydropyranyl, piperazinyl, and the like.

Thus, in accordance with the foregoing, the amide group or groups can be derived from compounds which are themselves antibacterial. Examples of such compounds that might be mentioned are 6-aminopenicillanic acid, 7-aminocephalosporanic acid, sulfa compounds such as sulfanilamide, sulfadiazine, sulfamerizine, sulfamethazine, sulfadimetine, sulfapyridine, sulfathiazole, sulfisoxazole, thiodiazole, sulfacetamide, sulfaguanidine, sulfaquinoxaline, and p-aminophenylsulfonamide, and p-aminobenzenesulfonic acid, antibiotic agents such as ampicillin, streptomycin, dihydrostreptomycin, cycloserine, cephaloglycin, cephalixin, and the like.

Those compounds of Formula I which are acidic, i.e. the free acids, may form salts, and such salts constitute a preferred aspect of the invention because they are more stable than the free acid. As will be appreciated by those skilled in this art, the compounds of Formula I where at least one of Y and Z is $-OH$ or $-SH$ will form organic and inorganic salts, and both are contemplated by this invention. Examples of such salts are inorganic metallic salts such as the sodium, aluminum, potassium, ammonium, calcium, magnesium, silver and iron salts. Organic salts that may be mentioned as representative include the salts with primary, secondary or tertiary amines such as monoalkylamines, dialkylamines, trialkylamines and nitrogen-containing heterocyclic amines. Representative examples are salts with amines such as α-phenethylamine, diethylamine, quinine, brucine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, esters of amino acids, and N-methylglucamine. If desired, the basic moiety of the salt may be a biologically-active amine such as erythromycin, oleandomycin or novobiocin.

The monoamide-monoester derivatives and particularly those compounds having a labile ester substituent are especially valuable derivatives. By the term "labile ester" as used herein is meant a group which is readily hydrolyzed biologically, for example by enzymes in the body fluids of animals including man, to produce the free acid or a salt thereof which is more active as an antibiotic agent. The amide or substituted amide groups present in the amide-ester derivatives are also readily hydrolyzed biologically in the body fluids and hence the amide-labile ester derivatives are useful in antibiotic therapy.

The esters which are sufficiently labile for use as antibiotic agents are readily determined experimentally, for example by incubation with body fluids, to ascertain whether or not under such conditions the ester group is cleaved. Alternatively, other methods, including chemical tests, can be utilized to determine if particular ester groups are sufficiently labile. Thus, the esters which give demonstrable antibiotic activity after heating in an aqueous medium at 37°C. for 2 hours at pH 2.2 or in an aqueous medium at pH 9 for 80 hours can be considered to be labile esters. Suitable labile ester groups that might be mentioned are ethers of the formula —$CH_2OR$, a phenacyloxymethyl group, acyloxy methyl groups of the formula —$CH_2OA$ wherein A is an acyl group comprising an organic radical derived from an organic acid by the removal of the hydroxy group, amide and substituted amide derivatives of such acyloxy methyl substituents, acylaminomethyl groups of the formula —$CH_2NHA$ wherein A is the same as defined above, thiomethyl ethers of the formula —$CH_2SR$, an ethynyloxy group of the formula —$CH_2OC \equiv CH$, substituted ethynyloxy groups of the formula —$CH_2OC \equiv CR$, a vinyloxymethyl group of the formula —$CH_2OCH=CH_2$, substituted vinyloxymethyl groups of the formulas —$CH_2OCH=CHR$ or —$CH_2OCH=CRR$, or a nitro oxy group of the formula —$CH_2ONO_2$. R in each of the foregoing formulas is a hydrocarbyl group or substituted hydrocarbyl group defined above.

Specific examples of such labile ester groups that might be mentioned are methoxymethyl, tetrahydropyranyloxomethyl, phenacyloxymethyl, acetoxymethyl, butyryloxymethyl, isobutyryloxymethyl, pivaloyloxymethyl, benzoyloxymethyl, 2-methylbenzoyloxymethyl, 2,6-dimethylbenzoyloxymethyl, 2-methyl-6-chlorobenzoyloxymethyl, 3-trifluoromethylbenzoyloxymethyl, 2-nitrobenzoyloxymethyl, 2-methylthiobenzoyloxymethyl, 2-thienylcarbonyloxymethyl, 2-furylcarbonyloxymethyl, 3-pyridylcarbonyloxymethyl, pyrazinylcarbonyloxymethyl, 2-methylcyclopentylcarbonyloxymethyl, 1-adamantylcarbonyloxymethyl, phenylsulfonylmethyl, phosphonooxymethyl, diethylphosphonooxymethyl, carbethoxyoxymethyl, carbamoyloxymethyl, N-methylcarbamoyloxymethyl, N,N-dimethylcarbamoyloxymethyl, phenylsulfamoyloxymethyl, acetaminomethyl, benzoylaminomethyl, methylthiomethyl, phenylthiomethyl, vinyloxymethyl, 1-methylvinyloxymethyl, and nitrooxymethyl. Thus, (—)(cis-1,2-epoxypropyl)phosphonamidic acid and (—)(cis-1,2-epoxypropyl)phosphonamidothioic acid or N-substituted derivatives thereof having a labile ester group or type shown above are especially useful derivatives.

Some representative examples of the compounds of Formula I above and salts thereof which can be prepared by the hereinafter-described processes that might be mentioned are:

1. Cyclic phosphonic acid diamides: P-(—)(cis-1,2-epoxypropyl)N,N'-dimethyl-N,N'-ethylenephosphonic diamide, P-(—)(cis-1,2-epoxypropyl)-N,N'-diethyl-N,N'-ethylenephosphonic diamide, P-(—)(cis-1,2-epoxypropyl)-N,N'-diphenyl-N,N'-ethylenephosphonic diamide, P-(—)(cis-1,2-epoxypropyl)-N,N'-dimethyl-N,N'-propylenephosphonic diamide, P-(—)(cis-1,2-epoxypropyl)-N,N'-diphenyl-N,N'-propylenephosphonic diamide, P-(—)(cis-1,2-epoxypropyl)-N,N'-diethyl-N,N'-butylenephosphonic diamide, P-(—)(cis-1,2-epoxypropyl)-N,N'-diphenyl-N,N'-butylenephosphonic diamide and the corresponding phosphonothioic acid amides;

2. Phosphonic acid diamides: P-(—)(cis-1,2-epoxypropyl)-N,N,N',N'-tetramethylphosphonic diamide, P-(—)(cis-1,2-epoxypropyl)-N,N,N',N'-tetraethylphosphonic diamide, P-(—)-(cis-1,2-epoxypropyl)-N,N,N',N'-tetrabenzylphosphonic diamide, P-(—)(cis-1,2-epoxypropyl)-N,N'-dimethyl-N,N'-diethylphosphonic diamide and the corresponding phosphonothioic acid amides;

3. Phosphonic acid diamides, amides and amine salts: (—)-(cis-1,2-epoxypropyl)-dimorpholinophosphinous acid, (—)(cis-1,2-epoxypropyl)-dipyrrolidinophosphinous acid, (—)(cis-1,2-epoxypropyl)-morpholinophosphinic acid morpholine salt, (—)(cis-1,2-epoxypropyl)-pyrrolidinophosphinic acid pyrrolidine salt and the corresponding phosphonothioic acid, diamides, amides and amine salts;

4. Phosphonamidothioates: S-benzyl-N,N-dimethyl-(—)-(cis-1,2-epoxypropyl)-phosphonamidothioate, S-methyl-N,N-diphenyl-(—)(cis-1,2-epoxypropyl)-phosphonamidothioate, S-isopropyl-(—)(cis-1,2-epoxypropyl)-phosphonoamidothioate and the corresponding phosphonamidodithioates;

5. Phosphonamidic halides: N,N-dimethyl-(—)(cis-1,2-epoxypropyl)-phosphonamidic chloride, N,N-diethyl-(—)(cis-1,2-epoxypropyl)-phosphonamidic chloride and the corresponding phosphonamidothioic acid compounds;

6. Phosphonamidates: benzyl-P-(—)(cis-1,2-epoxypropyl)-N,N-diethylphosphonamidate, ethyl-P-(—)(cis-1,2-epoxypropyl)-N,N-diphenylphosphonamidate, and allyl-P-(—)(cis-1,2-epoxypropyl)-N,N-di-(2-hydroxyethyl)-phosphonamidate and the corresponding phosphonamidothioates.

The phosphonamidates and diamides can be prepared by converting (—)(cis-1,2-epoxypropyl)phosphonic acid compound to its acid halide and then reacting the acid halide with a primary or secondary amine, or by reacting the (—)-(cis-1,2-epoxypropyl)phosphonic acid compound with a primary or secondary amine in the presence of a carbodiimide. Examples of such amines are dimethylamine, morpholine, dimethylethylenediamine, cyclohexylamine, dimethylpropylenediamine, benzylamine, hexamethylenediamine, diphenylamine, phenylamine and the like. Also contemplated are substituted amines such as chlorophenylamine, aminoethylbenzene, β-ethoxyethylmorpholine, diethoxyethylamine, p-methoxybenzylamine, p-nitrodiphenylamine, phenethylamine and the like.

Where the acid halide method is employed to prepare the compounds of Formula II below

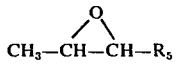  (II)

wherein $R_5$ is

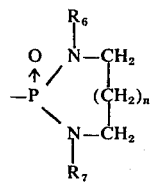

where $R_6$ and $R_7$ are hydrogen or loweralkyl such as methyl, ethyl, propyl, and butyl; aralkyl such as benzyl and substituted benzyl; aryl such as phenyl; and substituted phenyl such as halophenyl and nitrophenyl; and n is an interger from 0–2, the (−)(cis-1,2-epoxypropyl)phosphonic acid compound is first converted to the acid halide by reaction with a halogenating agent. Reagents such as phosphorous trichloride, phosphorous pentachloride, thionyl fluoride, thionyl chloride, or thionyl bromide may be used as the halogenating agent. It is preferred, however, to use reagents such as thionyl chloride and thionyl bromide to prepare the acid halides since these reagents tend to give better yields of the acid halide. The phosphonic acid compound may be employed as the free acid, but it is preferred to run the reaction with a salt of the phosphonic acid compound such as an amine salt or a metal salt. Suitable solvents for the reaction are hydrocarbons such as benzene, toluene, or a solvent such as chloroform. The reaction may be conveniently carried out in amine solvents such as pyridine, triethylamine, tri-n-propylamine, and the like. Where an amine is employed as the solvent, the amine serves as a solvent for the phosphonic acid compound and for the acid halide reaction, as well as a neutralizer for the hydrohalide formed. The product of the halogenation reaction is a di-acid halide, and the acid halide is then reacted with a diamine such as, for example, diethylethylenediamine, generally at ice bath temperatures, to form a cyclic phosphonic diamide. The phosphonic acid diamide is then isolated by techniques known in the art.

Where Z in Formula I is —OR or halogen and X is oxygen, the phosphonamidate is prepared by first reacting (−)(cis-1,2-epoxypropyl)phosphonic acid or a salt thereof with a salt of a heavy metal such as silver nitrate or gold nitrate. The di- metal salt is then reacted with an alkyl halide such as methyl or ethyl iodide to form a diester. The diester is partially hydrolyzed by treating it with an alkali such as sodium hydroxide to form a half ester-half salt such as, for example, the sodium salt of methyl-(−)-(cis-1,2-epoxypropyl)phosphonate, and the half ester-half salt is converted to the mono-acid halide-ester by reaction with, for example, thionyl chloride. The mono-acid halide-ester is then reacted with an amine such as, for example, dimethyl- amine to form those compounds where Z in Formula I is —OR, wherein R is a hydrocarbyl radical, and Y is —NR₁R₂.

Those compounds of Formula I where Z is —OH are prepared by reacting the phosphonamidate ester prepared above with about one equivalent of alkali such as sodium hydroxide. The sodium salt thus formed may then be converted to the free acid by techniques known in the art.

Where Z in Formula I is halo, the phosphonamidic halides can be prepared by converting the phosphonamidate salt, where Z is —OH, to its acid halide by reaction with a halogenating agent such as, for example, thionyl chloride.

Where Z in Formula I is —SH, the phosphonamide thioates can be prepared by converting a phosphonoamidate salt, where Z is —OH, to its acid halide by reaction with a halogenating agent such as, for example, thionyl chloride and then reacting the acid halide with potassium hydrogen sulfide.

Where Z in Formula I is —SR, the phosphonamidothioates can be prepared by reacting the phosphonamidic halide prepared above with a mercaptan such as, for example, methyl or ethyl mercaptan.

Where the carbodiimide method is employed to prepare the phosphonamidates and diamides, the (−)(cis-1,2-epoxypropyl)phosphonic acid compound is reacted with the amine in a suitable solvent in the presence of a carbodiimide such as, for example, dicyclohexylcarbodiimide. The phosphonic acid compound can be employed as the free acid, but it is preferred to run the reaction with a salt of the phosphonic acid such as an amine or metal salt. The carbodiimide is generally added to the solution of the phosphonic acid compound and the amine. Suitable solvents for the reaction are solvents such as acetone, dimethylformamide, dioxane, and tert.-butanol, and mixtures of the above with water. The reaction can be carried out at room temperature, but it is preferred to carry out the reaction at 50°–90°C., and preferably at the reflux temperature of the solvent employed. The phosphonamidate is then separated from the reaction mixture by techniques known in the art. Only the mono-amide can be prepared by this reaction. The di-amide can be prepared by repeating the reaction using a second equivalent of the amine. Where the reaction is repeated and a different amine is employed, it is then possible to prepare those compounds of Formula I where Y and Z are different —NR₁R₂ groups.

The various nitrogen and thio derivatives of (−) (cis-1,2-epoxypropyl)phosphonic acid of this invention can also be prepared from di-acid halides of the formula

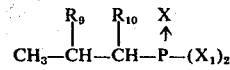

wherein one of $R_9$ and $R_{10}$ is a leaving group such as halo and the other is an oxygen-containing substituent which will undergo ring closure to form an epoxy nucleus. Halo leaving groups, especially chloro, are particularly preferred as are hydroxy or acyloxy ring closing groups. X is oxygen or sulfur and $X_1$ represents a halide, particularly chlorine or bromine.

The above compound is prepared from threo isomers of the formula

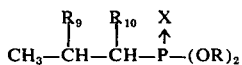

where X is oxygen and R, $R_9$ and $R_{10}$ are as previously defined, by halogenation using a suitable agent, particularly thionyl halide. When R is other than hydrogen or a salt, the ester must first be hydrolyzed, for example, by an acid such as a mineral acid.

Thio di-acid halides are preferably prepared by first acylating, where necessary, with acetyl halide or the like, to block the oxygen-containing substituent capable of ring closure, then halogenating as previously to prepare the di-acid halide, and then by treatment with $P_2S_5$ replacing the oxygen atom of the phosphonyl moiety with sulfur.

Diamides are prepared by treating the di-acid halide with four equivalents of a primary or secondary amine to form diamides of the formula

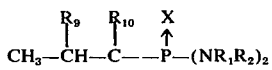

where the oxygen-containing substituent $R_9$ or $R_{10}$ is acyloxy.

Ring closure of the $R_9$ and $R_{10}$ groups is done by treating the diamide with a base such as pyridine, sodium hydroxide or the like to close the ring by displacing the leaving group, thus forming the epoxy portion of the ring.

In preparing epoxypropylphosphonic acid dihalides of the formula

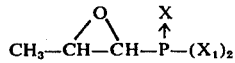

it is preferred to form the di-acid halide by treating epoxy acid or a salt with a mixture of thionyl chloride and pyridine.

In describing the acid halides obtained by reacting the phosphonic acid with a thionyl halide, they have been indicated to have the structure shown above. This is based on our present knowledge of these products and does not exclude the possibility that subsequent experimental data will establish that the structures are incorrect and that the group attached to the phosphorous is —SOCl which would react as a halide group and would be replaced, for example, with an amide group upon reaction with a primary or secondary amine. Accordingly, we do not wish to be bound by the indicated structures of the intermediate halides however likely they may appear to be in the light of our present knowledge. These explanations are presented principally as a means for providing a better understanding of our invention.

Amino acid conjugates of the general formula

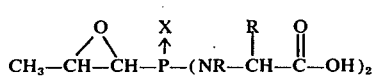

are prepared by treating the di-acid halide with an amino acid compound of the formula

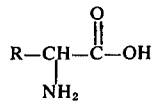

where R is a naturally occurring amino acid substituent.

Bis imides of the formula

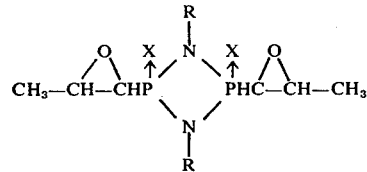

are prepared by reacting one equivalent of the di-acid halide with one equivalent of a primary amine of the formula $RNH_2$. R is preferably aryl, aralkyl or loweralkyl such as benzyl, p-chlorophenyl, methyl and the like.

Alkoxy substituted amides of the formula

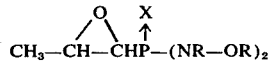

are prepared by treating the di-acid halide with a hydroxylamine of the formula NHROR where R is hydrogen or preferably aryl, aralkyl or lower alkyl.

Dihydrazides of the formula

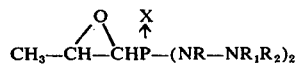

are prepared from the di-acid halide by treating the halide with a hydrazine of the formula $NHR—NR_1R_2$.

Compounds of the general formula

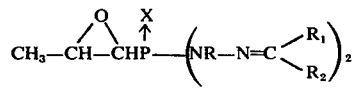

are prepared by treating the dihydrazide with a ketone of the formula

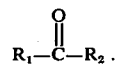

Compounds of the formula

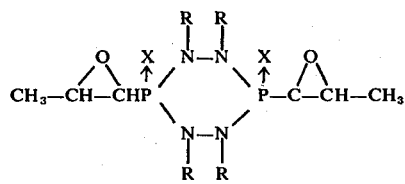

are prepared from the dihydrazide, where at least one of $R_1$ and $R_2$ is hydrogen, by adding an equivalent amount of di-acid halide to the hydrazide.

Azides of the general formula

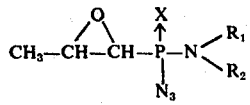

are prepared by reaction of a phosphonamide halide with an inorganic azide.

Guanidides of the formula

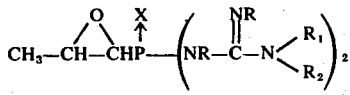

are prepared by reacting four equivalents of a quanidine of the formula

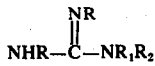

with a di-acid halide.

Cyanates and thiocyanates of the formula

where X is O or S and each X may be the same or different, are prepared by reacting a cyanate or thiocyanate such as the silver or lead salt with the di-acid halide.

Diurethanes and thiourethanes of the formula

are prepared by treating the cyanate or thiocyanate with an alcohol or mercaptan of the formula RXH where X is O or S and each X may be the same or different.

Diureides and thioureides of the formula

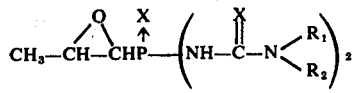

are prepared by treating the isocyanate or thiocyanate with an amine of the formula $NHR_1R_2$.

Unless otherwise noted, the substituents R, $R_1$, $R_2$, $R_6$, $R_9$, $R_{10}$, X and $X_1$ used in the preceding formulas are as previously defined.

The preceding compounds are prepared, unless otherwise noted, by simply mixing the reactants together with cooling where necessary to control exothermic reactions. The cyanates and thiocyanates are simply mixed with an equimolar (2X) amount of alcohol, mercaptan or amine and allowed to stand at room temperature.

(—) (Cis-1,2-epoxypropyl)phosphonic acid and its salts which are the starting materials in the preparation of the novel phosphonamidates and thioates can be prepared by aerobic fermentation of suitable aqueous nutrient media under controlled conditions by certain strains of the genus Streptomyces such as *Streptomyces fradiae* (MA-2915, NRRL-3417), *Streptomyces viridochromogenes* (MA-2903, NRRL-3413), and *Streptomyces wedmorensis* (MA-3269, ATCC-21239). The fermentation is carried out at temperatures ranging from about 25°–38°C. The pH of the nutrient media suitable for growing the Streptomyces and producing the phosphonic acid compound can vary from about 5.5–7.5. (—) (Cis-1,2-epoxypropyl)phosphonic acid may then be isolated from the fermentation broth by adsorption on either basic or acid-washed alumina. The adsorbed material can be eluted from the alumina by aqueous or aqueous alcoholic ammonium hydroxide solution having a pH of about 11.2 and fractionally collecting the eluate. The ammonium salt is obtained in this way. Other salts may be obtained by passing a solution of the ammonium salt over an appropriate cation exchange resin or by other techniques known in the art.

An alternative for obtaining the (—) cis1,2epoxypropyl)phosphonic acid derivatives of this invention is to treat threo (1,2-disubstituted propyl)phosphonic acid, its salts or esters under conditions suitable for affecting epoxide-type ring closure. One of the substituents in the 1 or 2-position of the propylphosphonic acid reactant IX must be a hydroxy radical or other functionally equivalent oxygen-containing substituent which will undergo ring closure to form the epoxide nucleus; the remaining substituent may be any leaving group which under the conditions of the reaction can be displaced to yield the desired epoxide product X

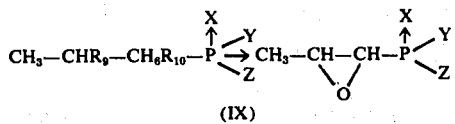

(IX)

wherein X, Y and Z are as previously defined; and $R_9$ and $R_{10}$ are hydroxy, halo, for example, chloro, bromo, iodo and the like; azido, loweralkanoyloxy, for example, acetoxy, propionyloxy and the like; trihalomethyl substituted loweralkanoyloxy such as trichloroacetoxy, trifluoroacetoxy, 3,3,3-trifluoropropionyloxy, 3,3,3-trichloropropionyloxy and the like; hydrocarbylsulfonyloxy such as loweralkanesulfonyloxy, for example, methanesulfonyloxy, ethanesulfonyloxy and the like; arylsulfonyloxy, for example, phenylsulfonyloxy and the like; alkarylsulfonyloxy, for example, tolylsulfonyloxy and the like; aralkylsulfonyloxy, for example, benzenesulfonyloxy and the like; aroyloxy, for example, benzoyloxy, 4-toluyloxy, 2-naphthoyloxy and the like; aralkanoyloxy, for example, benzylcarbonyloxy, naphthylcarbonyloxy and the like; tri-lower alkylammonium, for example, trimethylammonium, triethylammonium and the like; N-cycloalkyl di-lower alkylammonium wherein the cycloalkyl radical is mononuclear cycloalkyl containing 5-6 nuclear carbon atoms such as cyclopentyl, cyclohexyl and the like and di-lower alkylsulfonium, for example, dimethylsulfonium, diethylsulfonium, di-n-butylsulfonium and the like; aryloxy, for example, phenoxy and the like; dialkoxy phosphino, for example, di-lower alkoxyphosphino such as diethoxyphosphino and the like; N-(alkanesulfonyl)alkylamino or N-(alkarylsulfonyl)cycloalkylamino wherein the cycloalkyl radical is mono-nuclear cycloalkyl containing from 5-6 nuclear carbon atoms, for example N-(p-toluenesulfonyl)cyclohexylamino and the like; at least one of which $R_9$ and $R_{10}$ radicals is hydroxy or other functionally equivalent oxygen-containing radical as, for example, an acyloxy group such as loweralkanoyloxy, trihalomethyl substituted loweralkanoyloxy, aroyloxy, aralkanoyloxy and the like; which, under ring closure conditions, will form the desired epoxide ring.

The (−) (cis-1,2-epoxypropyl)phosphonic acid and phosphonothioic acid amines of this invention are effective in inhibiting the growth of various microorganisms. In particular, the phosphonamidates and diamides inhibit the growth of such microorganisms as *Proteus vulgaris* and *Salmonella schottmuelleri*. The antibiotics can be used as disinfectants in washing eggs and areas subject to infection by Salmonella. The amidates and their salts are also useful as bactericides in various industrial applications such as, for example, in inhibiting undesirable bacterial growth in the white paper in paper mills and in paints such as polyvinyl acetate latex paint.

The (−) (cis-1,2-epoxypropyl)phosphonic acid and phosphonothioic acid amides are also useful in the treatment of diseases caused by bacterial infections in animals.

The novel derivatives of (−) (cis-1,2-epoxypropyl)phosphonic acid and phosphonothioic acid can be administered alone or in combination with other biologically active ingredients, especially with other antibacterial agents such as penicillin, streptomycin and novobiocin.

The following examples are given for purposes of illustration and not by way of limitation:

EXAMPLE 1
P-(−)
(CIS-1,2-EPOXYPROPYL)-N,N'-DIMETHYL-N,N'-ETHYLENEPHOSPHONIC DIAMIDE

Dowex 50 (H⁺) cation exchange resin (20 g.) is washed well in ethanol. The resin is then suspended in methanol, and the suspension is cooled to 0°C. The phenethylamine salt of (−) (cis-1,2-epoxypropyl)phosphonic acid (2 g.) is dissolved in 15–20 ml. of methanol, and the resulting solution is cooled to 0°C. The salt solution and the resin suspension are mixed together and shaken vigorously for 60 seconds, and the mixture is filtered into 10 ml. of methanol containing 2 equivalents of pyridine. Excess pyridine is added to the filtrate, and the solution is evaporated to near dryness. The evaporation is repeated twice adding additional pyridine each time. The pyridine solution is then cooled to 0°C. in an ice bath, and to this solution is added with stirring 2 equivalents plus a 10% excess of thionyl chloride. After the addition is complete, the ice bath is removed and the solution is allowed to stir at room temperature for one hour. The solution of the diacid chloride is then transferred to an addition funnel and is added slowly to 2 equivalents of N,N'-dimethylethylenediamine in 30 ml. of benzene at ice bath temperatures. After the addition is complete, the ice bath is removed and the mixture is allowed to stir for one hour at room temperature. The mixture is then filtered and the filtrate is evaporated to dryness. Aliquots of toluene are added and evaporated off several times in order to remove traces of pyridine. The resulting residue is triturated with ether and, upon evaporation of the ether, 660 mg. of a dark oil is obtained. The oil is chromatographed on silica gel (18 g.) in chloroform. After the first yellow band comes off the column, the solvent is changed to 1% methanol-chloroform and 50 ml. portions are collected. Four fractions are collected, and Fraction No. 4 (210 mg.) upon tube distillation yields 200 mg. of P—P-(−) (cis-1,2-epoxypropyl)-N,N'-dimethyl-N,N'-ethylenephosphonic diamide, which is characterized by NMR and mass spectroscopy and thin layer chromatography.

When in the above procedure diethylethylenediamine, diphenylethylenediamine and phenylenediamine are employed in place of dimethylethylenediamine, P-(−) (cis-1,2-epoxypropyl)-N,N'-ethylenephosphonic diamide, P-(−) (cis-1,2-epoxypropyl)-N,N'-diphenyl-N,N'-ethylenephosphonicdiamide, and P-(−) (cis-1,2-epoxypropyl)-N,N'-(o-phenylene)-phosphonic diamide, respectively, are obtained.

EXAMPLE 2
SODIUM-P-(−)
(CIS-1,2-EPOXYPROPYL)-N,N-DIMETHYLPHOSPHONAMIDATE

Phenethylammonium-(−) (cis-1,2-epoxypropyl)phosphonate (62 g.) is placed in 390 ml. of water containing sodium bicarbonate (18.8 g., 1 equivalent). To the resulting solution is added dropwise with stirring an aqueous solution of silver nitrate (76.16 g., 2 equivalents). After the addition is complete, the resulting mixture is allowed to stir for 30 minutes at room temperature. The mixture is then filtered and washed well in water, acetone and ether. The disilver salt which is obtained (74 g.) is then suspended in 500 ml. of dimethoxyethane, and methyl iodide (64 g., 2 equivalents) is added to the suspension. The mixture is allowed to stir overnight at 50°–60°C., after which it is filtered and the filtrate is evaporated to dryness. The residue which contains the dimethyl ester (32 g.) is then chromatographed on 90 g. of silica-gel in chloroform. The dimethyl ester obtained from the chromatogram (18 g.) is dissolved in 50 ml. of water and 2.6 N sodium hydroxide (0.9 equivalents) is added slowly to this solution with stirring. The reaction mixture is allowed to stir overnight and is then evaporated to dryness. The residue contains 15.7 g. of half ester-half salt and 1.3 g. of diester. The half ester-half salt (3 g.) is suspended in 100 ml. of benzene with stirring, and the suspension is cooled in an ice bath. Thionyl chloride (1 equivalent plus 10% excess) is added to the suspension, and the mixture is allowed to stir at room temperature for one hour after the addition is complete. The mixture is then cooled in an ice bath and a large excess of dimethylamine is bubbled into the mixture. The stirring and cooling are continued for one-half hour after the addition is complete, and for one-half hour at room temperature. The mixture is then filtered, and the filtrate is evaporated to dryness. The light yellow oil (12 g.) which is obtained upon evaporation of the filtrate is chromatographed on 360 g. on silica-gel in chloroform. Fraction Nos. 7 through 14 (2.2 g.) are combined and, upon tube distillation, a light yellow oil (2 g.) containing the half amide-half ester is obtained. The half amide-half ester (1 g.) is then dissolved in 25 ml. of water, and 2.6 N sodium hydroxide (0.95 equivalents) is added. The solution is then stirred overnight at room temperature. Upon lyophilization of the solution, 600 mg. of sodium P-(−)(cis-1,2-epoxypropyl)-N,N-dimethylphosphonamidate is obtained and is characterized by NMR.

When in the above procedure dimethylamine, dibutylamine, and diphenylamine are employed in place of dimethylamine, sodium P-(−)(cis-1,2-epoxypropyl)-N,N-diethylphosphonamidate, sodium P-(−) (cis-1,2-epoxypropyl)-N,N-dibutylphosphonamidate, and sodium P-(−) (cis-1,2-epoxypropyl)-N,N-diphenylphosphonamidate, respectively, are obtained.

EXAMPLE 3

P-(−)(CIS-1,2-EPOXYPROPYL)-N,N,N',N'-TETRAMETHYLPHOSPHONIC DIAMIDE

Phenethylammonium-(−)(cis-1,2-epoxypropyl)-phosphonate (10 g.) is dissolved in 100 ml. of methanol, and the solution is cooled to 0°C. Dowex 50 ($H^+$) cation exchange resin (100 g.) is washed well in methanol. The resin is then suspended in methanol, and the suspension is cooled to 0°C. The suspension of the cation exchange resin and the solution of the salt are mixed together and shaken vigorously for 60 seconds after which the mixture is filtered into 20 ml. of methanol containing 2 equivalents of pyridine. After filtration, excess pyridine is added, and the filtrate is evaporated to dryness. The evaporation is repeated twice adding additional pyridine each time. The pyridine solution is then cooled to 0°C. in an ice bath, and thionyl chloride (2 equivalents plus 10% excess) is added with stirring. After the addition is complete, the ice bath is removed and the solution is allowed to stir for one hour at room temperature. The solution is then cooled in an ice bath, and a large excess of dimethylamine is bubbled into the pyridine solution. After the addition of the dimethylamine is complete, the ice bath is removed and the mixture is allowed to stir for one hour at room temperature. The mixture is filtered and evaporated to dryness. Aliquots of toluene are added and evaporated off several times in order to remove traces of pyridine. The residue obtained is triturated with ether and contains 2.5 g. of crude red oil. The oil is chromatographed on 50 g. of silica-gel in 5% methanol-chloroform. The red oil (2 g.) obtained from the chromatogram is tube distilled, and P-(−)(cis-1,2-epoxypropyl)-N,N,N',N'- tetramethylphosphonic diamide (1.25 g.) is obtained as a light yellow oil and is characterized by thin layer chromatography and elemental analysis.

When in the above procedure dibutylamine, methylethylamine, and dibenzylamine are employed in place of dimethylamine, P-(−)(cis-1,2-epoxypropyl)-N,N,N',N'-tetrabutylphosphonic diamide, P-(−)(cis-1,2epoxypropyl)-N,N'-dimethyl-N,N'-diethylphosphonic diamide, and P-(−)-(cis-1,2-epoxypropyl)-N,N,N',N'-tetrabenzylphosphonic diamide, respectively, are obtained.

EXAMPLE 4

(−)(CIS-1,2-EPOXYPROPYL)-DIMORPHOLINOPHOSPHINOUS ACID

Phenethylammonium-(−)(cis-1,2-epoxypropyl)-phosphonate (10 g.) is dissolved in 100 ml. of methanol, and the solution is cooled to 0°C. Dowex 50 ($H^+$) cation exchange resin (100 g.) is washed well in methanol. The resin is then suspended in methanol and the suspension is cooled to 0°C. The suspension of the cation exchange resin and the solution of the salt are mixed together and shaken vigorously for 60 seconds, after which the mixture is filtered into 20 ml. of methanol containing 2 equivalents of pyridine. After filtration, excess pyridine is added and the filtrate is evaporated to dryness. The evaporation is repeated twice adding additional pyridine each time. The pyridine solution is then cooled to 0°C. in an ice bath, and thionyl chloride (2 equivalents plus 10% excess) is added with stirring. After the addition is complete, the ice bath is removed and the solution is allowed to stir for one hour at room temperature. The pyridine solution of the di-acid chloride is then cooled again in an ice bath, and freshly distilled morpholine (4 equivalents) is added slowly. After the addition is complete, the mixture is stirred at room temperature for 1 hour. The mixture is then filtered, and the filtrate is evaporated to dryness. Traces of pyridine are removed by the addition and removal of toluene, and the residue is triturated with ether. About 10 g. of residue is obtained. The above regeneration is divided into five 2-gram runs, is regenerated, and followed completely through on five parallel runs to yield 200 mg. of a viscous oil which crystallizes slowly. The 200 mg. is obtained from about 25 g. of crude reaction product which is chromatographed on 750 g. of silica-gel in 10% methanol-chloroform. The fore and hind running materials from the column are combined to yield an additional 50 mg. of material. The combined 250 mg. of reddish solid is triturated with warm ether, and upon evaporation of the ether, (−)(cis-1,2-epoxypropyl)-dimorpholinophosphinous acid (230 mg.) is obtained as a light yellow solid and is characterized by thin layer chromatography and NMR.

When in the above procedure cyclohexylamine and aniline are employed in place of morpholine, P-(−)(cis-1,2-epoxypropyl)-N,N-diphenylphosphonic diamide, and P-(−)(cis-1,2-epoxypropyl)-N,N'-dicyclohexylphosphonic diamide, respectively, are obtained.

EXAMPLE 5

(−)(CIS-1,2-EPOXYPROPYL)-MORPHOLINO-PHOSPHINIC ACID MORPHOLINE SALT

Phenethylammonium-(−)(cis-1,2-epoxypropyl)-phosphonate (2.59 g.) is passed through an ice-water jacketed column of Dowex 50 ($H^+$) resin (40 g.) and is eluted with ice water. The eluent (450 ml.) is immediately neutralized with freshly treated morpholine (860 mg.), and the aqueous solution is lyophilized.

A solution of dicyclohexylcarbodiimide (8.24 g.) in 150 ml. of t-butanol is added dropwise to a refluxing solution of the lyophilized material, 100 ml. of t-butanol, 100 ml. of water, and 2.61 ml. of morpholine during 3 hours. After the addition is complete, the refluxing is continued for an additional hour. The reaction mixture is then cooled to room temperature and is filtered free of dicyclohexylurea. The filter cake is washed with t-butanol and the filtrate is evaporated in vacuo until all of the t-butanol is removed. The aqueous solution is extracted 3 times with ether, and upon lyophilization of the aqueous solution, (−)(cis-1,2-epoxypropyl)-morpholinophosphonic acid morpholine salt is obtained.

When in the above procedure dimethylamine, diphenylamine, cyclohexylamine, and pyrrolidine are employed in place of morpholine, dimethylammonium-P-(−)(cis-1,2-epoxypropyl)-N,N-dimethylphosphonamidate, diphenylammoniumP-(−)(cis-1,2-epoxypropyl)-N,N-diphenylphosphonamidate, cyclohexylammonium-P-(−)(cis-1,2-epoxypropyl)-N-cyclohexylphosphonate, and (−)(cis-1,2-epoxypropyl)-pyrrolidinophosphinic acid pyrrolidine salt, respectively, are obtained.

EXAMPLE 6

METHYL P-(—)(CIS-1,2-EPOXYPROPYL)-N,N-DIMETHYL PHOSPHONAMIDATE

Phenethylammonium-(—)(cis-1,2-epoxypropyl)-phosphonate (62 g.) is placed in 390 ml. of water containing sodium bicarbonate (18.8 g., 1 equivalent). To the resulting solution is added dropwise with stirring an aqueous solution of silver nitrate (76.16 g., 2 equivalents). After the addition is complete, the resulting mixture is allowed to stir for 30 minutes at room temperature. The mixture is then filtered and washed well with water, acetone and ether. The disilver salt which is obtained (74 g.) is then suspended in 500 ml. of dimethoxyethane, and methyl iodide (64 g., 2 equivalents) is added to the suspension. The mixture is allowed to stir overnight at 50°-60°C., after which it is filtered and the filtrate is evaporated to dryness. The residue which contains the dimethyl ester (32 g.) is then chromatographed on 90 g. of silica-gel in chloroform. The dimethyl ester obtained from the chromatogram (18 g.) is dissolved in 50 ml. of water and 2.6 N sodium hydroxide (0.9 equivalents) is added slowly to this solution with stirring. The reaction mixture is allowed to stir overnight and is then evaporated to dryness. The residue contains 15.7 g. of half esterhalf salt and 1.3 g. of diester. The half ester-half salt (3 g.) is suspended in 100 ml. of benzene with stirring, and the suspension is cooled in an ice bath. Thionyl chloride (1 equivalent plus 10% excess) is added to the suspension, and the mixture is allowed to stir at room temperature for one hour after the addition is complete. The mixture is then cooled in an ice bath and a large excess of dimethylamine is bubbled into the mixture. The stirring and cooling are continued for one-half hour after the addition is complete, and for one-half hour at room temperature. The mixture is then filtered, and the filtrate is evaporated to dryness. The light yellow oil (12 g.) which is obtained upon evaporation of the filtrate is chromatographed on 360 g. of silica-gel in chloroform. Fractions Nos. 7 through 14 (2.2 g.) are combined and, upon tube distillation, methylP-(—)(cis-1,2-epoxypropyl)-N,N-diethylphosphonamidate is obtained as a light yellow oil, and is characterized by NMR.

EXAMPLE 7

N,N-DIMETHYL-(CIS-1,2-EPOXYPROPYL)-PHOSPHONAMIDIC CHLORIDE

Sodium-P-(—)(cis-1,2-epoxypropyl)-N,N-dimethylphosphonamidate (0.60 g.) is suspended in 50 ml. of benzene with stirring, and the suspension is cooled on an ice bath. Thionyl chloride (1 equivalent plus 10% excess) is added to the suspension, and the mixture is allowed to stir at room temperature for one hour after the addition is complete. Upon removal of the solvent, N,N-dimethyl-(cis-1,2-epoxypropyl)-phosphonamidic chloride is obtained.

EXAMPLE 8

S-BENZYL-N,N-DIMETHYL-(—)(CIS-1,2-EPOXYPROPYL)-PHOSPHONAMIDOTHIOATE

N,N-dimethyl-(cis-1,2-epoxypropyl)-phosphonamidic chloride (0.1 mole) is dissolved in 100 ml. of benzene together with 0.1 mole of triethylamine. The resulting mixture is cooled to 5°C. and to it is added 0.1 mole of benzylmercaptan at such a rate as to maintain the temperature at 5°-10°C. After the addition is complete, the mixture is stirred at room temperature for 1 hour. The precipitated triethylamine hydrochloride is then filtered off, and upon removal of the solvent, S-benzyl-N,N-dimethyl-(—)(cis-1,2-epoxypropyl)-phosphonamidothioate is obtained.

When in the above procedure ethylmercaptan, thiophenol and methylmercaptan are employed in place of benzylmercaptan, S-ethyl-N,N-dimethyl-(—)(cis-1,2-epoxypropyl)-phosphonamidothioate, S-phenyl-N,N-dimethyl-(—)(cis-1,2-epoxypropyl)-phosphonamidothioate, and S-ethyl-N,N-dimethyl-(cis-1,2-epoxypropyl)-phosphonamidothioate, respectively, are obtained.

EXAMPLE 9

(—)(CIS-1,2-EPOXYPROPYL)PHOSPHONIC DI-ACID CHLORIDE

Dowex 50 (H$^+$) cation exchange resin (20 g.) is washed well in ethanol. The resin is then suspended in methanol, and the suspension is cooled to 0°C. The (—) 1-$\alpha$-phenethylamine salt of (—)(cis-1,2-epoxypropyl)-phosphonic acid (2 g.) is dissolved in 15–20 ml. of methanol, and the resulting solution is cooled to 0°C. The salt solution and the resin suspenison are mixed together and shaken vigorously for 60 seconds, and the mixture is filtered into 10 ml. of methanol containing 2 equivalents of pyridine. Excess pyridine is added to the filtrate, and the solution is evaporated to near dryness. The evaporation is repeated twice adding additional pyridine each time. The pyridine solution is then cooled to 0°C. in an ice bath, and to this solution is added with stirring 2 equivalents plus a 10% excess of thionyl chloride. After the addition is complete, the ice bath is removed and the solution is allowed to stir at room temperature for one hour to give a solution of the di-acid chloride of (—) (cis-1,2-epoxypropyl)phosphonic acid.

EXAMPLE 10

N,N,'-BIS(1-CARBOXYETHYL)(—)(CIS-1,2-EPOXYPROPYL)PHOSPHONIC ACID DIAMIDE

Two equivalents of benzyl-L-alanine are added to a stirred (—)(cis-1,2-epoxypropyl)phosphonic di-acid chloride solution from Example 9, which is chilled in an ice bath. The mixture is stirred at room temperature for one hour, filtered and the filtrate concentrated in vacuo. The residue is dissolved in 30 ml. of methanol and 10% palladium on carbon (0.5 g.) is added. The mixture is hydrogenated at 40 p.s.i. for 15 minutes and the catalyst is filtered off. The solvent is removed in vacuo to give N, N'-bis(1-carboxyethyl)(—)(cis-1,2-epoxypropyl)phosphonic acid diamide.

When benzylglycine is reacted as above with the di-acid chloride of (—)(cis-1,2-epoxypropyl)phosphonic acid there is produced N,N'-bis'(1-carboxymethyl)(—)(cis-1,2-epoxypropyl)phosphonic acid diamide.

EXAMPLE 11

BIS-(−)(CIS-1,2-EPOXYPROPYL(PHOSPHONIC ACID N-PROPYLIMIDE

The di-acid chloride is prepared as in Example 9. Three equivalents of n-propylamine are added dropwise to the dichloride and the mixture is refluxed for one-half hour. The mixture is filtered and the filtrate is concentrated in vacuo to yield bis-(−)(cis-1,2-epoxypropyl)phosphonic acid n-propylimide.

When methylamine, benzylamine, allylamine are substituted for n-propylamine above, there is obtained the corresponding bis-(−)(cis-1,2-epoxypropyl)phosphonic acid methylimide, benzylimide and allylimide.

EXAMPLE 12

N,N'-DIMETHOXY(−)(CIS-1,2-EPOXYPROPYL)-PHOSPHONIC ACID DIAMIDE

Two equivalents of O-methylhydroxylamine are added to the (−)(cis-1,2-epoxypropyl)phosphonic di-acid chloride of Example 9 at ice-bath temperature and the reaction mixture is stirred at room temperature for one hour. The mixture is filtered and the filtrate concentrated to dryness to give N,N'-dimethoxy(−)(cis-1,2-epoxypropyl)-phosphonic acid diamide.

When O-ethylhydroxylamine is reacted with (−) (cis-1,2-epoxypropyl)phosphonic acid dichloride there is obtained N,N'-diethoxy(−)(cis-1,2-epoxypropyl)phosphonic acid diamide.

EXAMPLE 13

(−)(CIS-1,2-EPOXYPROPYL)PHOSPHONIC ACID DIHYDRAZIDE

The (−)(cis-1,2-epoxypropyl)phosphonic di-acid chloride is prepared as in Example 9 and is transferred to an addition funnel and is added slowly to 4 equivalents of 95% hydrazine in 5 ml. of ether at ice-bath temperature. The reaction mixture is concentrated in vacuo and the residue is treated with 5 ml. of hot ethanol, followed by filtration. The solid fraction obtained upon cooling the filtrate is hydrazine hydrate. Concentration of the mother liquors yields (−)(cis-1,2-epoxypropyl)phosphonic acid dihydrazide.

When $N^1$, $N^1$-dimethylhydrazine, $N^1$-methyl-$N^2$, $N^2$-diethylhydrazine, $N^1$,$N^1$-dibenzylhydrazine, $N^1$-phenylhydrazine is reacted as above with (−)(cis-1,2-epoxypropyl)-phosphonic acid dichloride there is produced $N^1$, $N^1$, $N^{1'}$, $N^{1'}$-tetramethyl-, $N^1$, $N^{1'}$-dimethyl-$N^2$,$N^2$,$N^{2'}$, $N^{2'}$-tetraethyl-, $N^1$,$N^1$,$N^{1'}$, $N^{1'}$-tetrabenzyl- and $N^1$, $N^{1'}$-diphenyl (−)(cis-1,2-epoxypropyl)phosphonic acid dihydrazide, respectively.

EXAMPLE 14

$N^2$, $N^{2'}$-DIMETHYLIDINE (−)(CIS-1,2-EPOXYPROPYL)PHOSPHONIC ACID DIHYDRAZIDE

Hot acetone is reacted directly with (−)(cis-1,2-epoxypropyl)phosphonic acid dihydrazide to give $N^2$, $N^{2'}$-dimethylidine (−)(cis-1,2-epoxypropyl)phosphonic acid dihydrazide. Reaction with acetophenone gives $N^2$, $N^{2'}$-phenylethylidine (−)(cis-1,2-epoxypropyl)phosphonic acid dihydrazide.

EXAMPLE 15

3,6-BIS-(−)(CIS-1,2-EPOXYPROPYL)HEXAHYDRO-1,2,4,5,3,6-TETRAAZODIPHOSPHOLANE-3,6-DIOXIDE

The (−) di-acid chloride is prepared as in Example 9 and is transferred to an addition funnel and is added slowly over a period of three hours to a well-stirred solution containing 1 equivalent of (−)(cis-1,2-epoxypropyl)phosphonic acid dihydrazide in 5 ml. toluene at room temperature. The solvent is removed in vacuo to give 3,6-bis-(−)(cis-1,2-epoxypropyl(hexahydro-1,2,4,5,3,6-tetraazodiphospholane-3,6-dioxide.

EXAMPLE 16

N,N-DIMETHYL (−)(CIS-1,2-EPOXYPROPYL)PHOSPHONAMIDIC AZIDE

N,N-dimethyl (−)(cis-1,2-epoxypropyl)phosphonamidic chloride (1.0 g.) and 355 mg. of sodium azide in 5.0 ml. of dry pyridine is heated under reflux for 18 hours. The solids are removed by filtration and the solvent is removed from the filtrate in vacuo to give N,N-dimethyl (−)(cis-1,2-epoxypropyl)phosphonamide azide.

EXAMPLE 17

(−)(CIS-1,2-EPOXYPROPYL)PHOSPHONODIGUANIDINE

Four equivalents of guanidine are added slowly to a stirred, chilled mixture of di-acid chloride of (−)(cis-1,2-epoxypropyl)phosphonic acid in benzene. After stirring for one-half hour at room temperature, the precipitate of guanidine hydrochloride is filtered off. The filtrate is evaporated in vacuo to give (−)(cis-1,2-epoxypropyl)phosphonodiguanidine. When guanidine is replaced by N,N',N''-trimethylguanidine, there is produced N,N,N', N',N'',N'',-hexamethyl (−)(cis-1,2-epoxypropyl(phosphonodiguanidine.

EXAMPLE 18

(−)(CIS-1,2-EPOXYPROPYL)PHOSPHONYL DIISOCYANATE

A suspension of 6.0 g. of silver cyanate in 20 ml. of acetonitrile is treated dropwise with 3.5 g. of (−)(cis-1,2-epoxypropyl)phosphonic acid dichloride in 10 ml. benzene. The mixture is stirred for one hour and filtered. The filtrate is concentrated to give (−)(cis-1,2-epoxypropyl)phosphonyl diisocyanate. When silver cyanate is replaced by silver thiocyanate there is produced (−)(cis-1,2-epoxypropyl)phosphonyl dithioisocyanate.

EXAMPLE 19

BIS-METHYL (−)(CIS-1,2-EPOXYPROPYL)PHOSPHONYL DIURETHANE

The bis-methylurethane is prepared by the addition of (−)(cis-1,2-epoxypropyl)phosphonyl diisocyanate to excess methanol. The resulting solution is evaporated to dryness and the product is recrystallized from methanol-ether to give bis-methyl (−)(cis-1,2-epoxypropyl)phosphonyl diurethane. When phenol or i-propyl mercaptan is reacted as above, there is produce bis-phenyl (−)(cis-1,2-epoxypropyl)phosphonyl diurethane and bis-S-isopropyl (—)(cis-1,2-epoxypropyl)-phosphonylthiourethane, respectively.

EXAMPLE 20

DIPHENYL (—)(CIS-1,2-EPOXYPROPYL)PHOSPHONYL DIUREIDE

The bis-phenylurea is prepared by addition of (—)(cis-1,2-epoxypropyl)phosphonyl diisocyanate to excess aniline. The resulting crude solid is washed thoroughly with 6-N hydrochloric acid, water and alcohol to give diphenyl (—)(cis-1,2-epoxypropyl(phosphonyl diureide. When (—)(cis-1,2-epoxypropyl)diisocyanate is reacted with excess diethylamine, there is obtained diethyl (—)(cis-1,2-epoxypropyl)phosphonyl diureide.

EXAMPLE 21

THREO 1-HYDROXY-2-BROMOPROPYLPHOSPONIC ACID

A. Dimethyl Threo 1-Hydroxy-2-Bromopropylphosphonate

A solution of dimethyl (—)(cis-1,2-epoxypropyl)-phosphonate (7 g.) in 300 ml. of chloroform is vigorously stirred with 50 ml. of 48% hydrobromic acid at room temperature for 2 hours. The chloroform layer is separated and the aqueous layer extracted three times with 50 ml. portions of chloroform. The combined chloroform extracts are evaporated and the partially crystalline mass stirred with a little ether and filtered, giving dimethyl threo 1-hydroxy-2bromopropylphosphonate (m.p. 65°–69°).

B. Threo 1-hydroxy-2-Bromopropylphosphonic Acid

A solution of dimethyl threo 1-hydroxy-2-bromo-propylphosphonate (0.5 g.) in 10 ml. of concentrated hydrochloric acid is heated on the steam bath for one and one-half hours. The solution is concentrated under reduced pressure and the residue redissolved in water and evaporated several times to remove excess hydrochloric acid. A final drying under high vacuum yields threo 1-hydroxy-2-bromopropylphosphonic acid as a heavy oil.

EXAMPLE 22

SODIUM (2-HYDROXY-1-BROMOPROPYL)PHOSPHONATE 10.8 g. of cis-propenylphosphonic acid is dissolved in 50 ml. of water and the pH of the solution is adjusted to 4.2 by the addition of 2.5 N sodium hydroxide. 13.8 g. of N-bromoacetamide is added and the suspension is stirred at room temperature. The reaction is complete when the N-bromoacetamide is in solution and the mixture is negative to starch-iodide paper. The solution is lyophilized and the residue is triturated several times with chloroform to give sodium (2-hydroxy-1-bromopropyl)-phosphonate.

The sodium salt of (2-hydroxy-1-bromopropyl)phosphonic acid (0.03 moles) obtained as described above is treated with 0.018 moles of quinine in 200 ml. of methanol. The solution is evaporated to a syrup and the residue dissolved in 50 ml. of methanol. The mixture is cooled and allowed to stand. Crystalline salt settled out of solution is slurried in methanol, filtered and washed with acetone to give the quinine salt of threo(2-hydroxy-1-bromopropylphosphonate) isomer which is converted to the sodium salt by reaction with dilute sodium hydroxide.

EXAMPLE 23

(1-BROMO-2-ACETOXYPROPYL)PHOSPHONIC ACID

One and one-half grams of (1-bromo-2-hydroxypropyl)phosphonic acid prepared from the sodium salt obtained in Example 22 is heated with 5 ml. of acetyl bromide for one hour. The excess acetyl bromide is distilled off under reduced pressure and ice-cold water is added to the residue. The solution is stirred at room temperature and lyophilized to give (1 bromo-2-acetoxypropyl)phosphonic acid.

In the same way threo 1-hydroxy-2-bromopropylphosphonic acid prepared as described in Example 21 is acetylated to obtain the 1-acetoxy derivative.

EXAMPLE 24

THREO (2-BROMO-1-ACETOXYPROPYL)PHOSPHONO-THIOIC DICHLORIDE

One and one-half grams of threo (2-bromo-1-acetoxypropyl)phosphonic acid prepared as described in Example 23 is added to 0.5 ml. of pyridine and the mixture evaporated to near dryness. The evaporation is repeated twice adding additional pyridine each time. The pyridine solution is cooled in an ice-bath and 2.1 equivalents of thionyl chloride is added slowly with stirring. The solution is then allowed to stir at room temperature for one hour before removing the solvent in vacuo to give threo (2-bromo-1-acetoxypropyl)-phosphonic dichloride.

One and one-quarter grams of (2-bromo-1-acetoxypropyl)phosphonic dichloride is heated with 0.55 g. of finely pulverized $P_2S_5$ under nitrogen at 130°C. for three hours. The reaction mixture is fractionally distilled to give threo (2-bromo-1-acetoxypropyl)phosphonothioic dichloride.

EXAMPLE 25

THREO P-(2-BROMO-1-ACETOXYPROPYL)-N,N,N',N'-TETRAMETHYLPHOSPHONOTHIOIC DIAMIDE ISOMER

A solution of 1 g. of (2-bromo-1-acetoxypropyl)-phosphonothioic dichloride (prepared as described in Example 24) in 10 ml. of pyridine is chilled in an ice bath and a large excess of dimethylamine is bubbled into the pyridine solution. The ice bath is removed and the mixture is allowed to stir at room temperature for one hour. The mixture is filtered and evaporated to dryness. Aliquots of toluene are added and evaporated off several times in order to remove traces of pyridine. The residue consists of threo P-(2-bromo-1-acetoxypropyl)-N,N,N',N'-tetramethylphosphonothioic diamide isomer.

EXAMPLE 26

P-(-) (CIS-1,2-EPOXYPROPYL)-N,N,N',N'-TETRAE-THYLPHOSPHONOTHIOIC DIAMIDE

One-half gram of threo P-(2-bromo-1-acetoxyethyl)-N,N,N',N'-tetraethylphosphonothioic diamide prepared as described in Example 25 is added to two equivalents of 2.5 N NaOH and allowed to stir at room temperature until the aqueous mixture is essentially neutral. The mixture is lyophilized and chromatographed on 20 g. of silica-gel using methanol-chloroform mixture as eluant. The product, obtained as an oil, is P-(-) (cis-1,2-epoxypropyl)-N,N,N'-N'-tetraethylphosphonothioic diamide.

The following is an illustration of a method of preparing the (-) (cis-1,2-epoxypropyl)phosphonic acid starting compounds.

A. A lyophilized culture of *Streptomyces fradiae* (MA-2913, ATCC-21099) is used to inoculate 50 ml. of sterile medium of the following composition in a 250 ml. baffled Erlenmeyer flask:

|  | grams/liter |
|---|---|
| Ground oatmeal | 10 |
| Yeast hydrolysate | 10 |
| MgSO$_4$.7H$_2$O | 0.05 |
| Phosphate buffer* | 2 ml. |
| *91 g. KH$_2$PO$_4$ and 95 g. Na$_2$HPO$_4$ made up to 1 liter with distilled water. | |
| Water q.s. | Balance |

The medium is adjusted to pH 6.5 prior to sterilization.

The inoculated flask is incubated at 28°C. for 24 hours on a rotary shaker. 10 Ml. of the resulting broth is used to inoculate a second 250 ml. Erlenmeyer flask containing 50 ml. of the same sterile medium. After incubation at 28°C. for 24 hours on a rotary shaker, the resulting fermentation broth is used to inoculate a 5 liter fermenter containing 3 liters of sterile nutrient broth of the following composition:

|  | grams/liter |
|---|---|
| Ground oatmeal | 30 |
| Distillers solubles | 10 |
| Soybean meal | 25 |
| Sodium citrate | 4 |
| Sodium ascorbate | 0.5 |
| Water q.s. | Balance |

The medium is adjusted to pH 65 before sterilizing.

The inoculated medium is then incubated at 28°C. for four days while agitating and aerating the fermentation broth with 3 liters of air per minute; 3 ml. of a propylene glycol polyer having a molecular weight of about 2,000 (sold under the trade name of Polyglycol P-2000 by the Dow Chemical Company) being added to prevent excessive foaming. The resulting fermentation broth has an activity of 5.9 units/ml. as determined by the standard assay using *Proteus vulgaris*.

A second fermentation using this same procedure results in a broth having an activity of 6.75 units/ml.

The broths from the two fermentations are combined and filtered. The resulting filtered broth contains 20 mg. of solids per ml. and at a dilution of 1 to 32 gives a 25 mm. zone of inhibition when tested against *Proteus vulgaris* using the modified assay procedure.

96.5 Ml. of the broth is stirred for 40 minutes with 2.5 g. of acid-washed alumina. The mixture is then filtered, and the filtrate is found to contain 20% of the activity. The filtered alumina adsorbate is washed and eluted with aqueous ammonia at a pH of 11.2. The eluate is evaporated to remove ammonia and is found to give a 25 mm. inhibition zone at a dilution of 0.125 mg./ml. by the modified assay procedure.

B. 10 Ml. of the aqueous solution of the ammonium salt off (-) (cis-1,2-epoxypropyl)phosphonic acid containing 200 mg. of solids is diluted to 50 ml. with water, and the resulting solution is passed through a column of 200 ml. (settled volume) of cation exchange resin (Dowex 50) on the (+)α-phenethylammonium cycle. After the initial eluate is collected, the column is rinsed with 200 ml. of water, and the total eluate collected is evaporated in vacuo to a volume of 100 ml. The pH of the concentrate is adjusted to 5.0 by careful addition of small portions of Dowex 50 resin on the acid cycle, and the acidic solution is filtered and evaporated to dryness in vacuo at room temperature. The residue is taken up into 100 ml. of methanol, and the methanol solution is filtered to remove inorganic salts. The filtrate is concentrated to a small volume, 100 ml. of isopropanol is added, and the evaporation is repeated until crystals form. The crystalline slurry is refrigerated for about 16 hours, and the crystalline product, (-) (cis-1,2-epoxypropyl)phosphonic acid mono-(+)α-phenethylammonium salt, is collected by filtration.

It should be understood that, although this invention has been described with reference to particular embodiments thereof, changes and modifications may be made which are within its intended scope, and it should be limited only by the language of the appended claims.

We claim:

1. A (−) compound of the formula

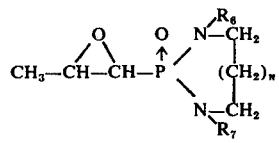

wherein R$_6$ and R$_7$ are loweralkyl and $n$ is an integer from 0–2.

2. The compound of claim 1 where $n$ is 0.

3. P-(-)-(cis-1,2-epoxypropyl) -N,N'-dimethyl-N,N'-ethylenephosphonic diamide.

* * * * *